(12) United States Patent
Gillisen-Van Der Vight et al.

(10) Patent No.: US 11,891,726 B2
(45) Date of Patent: *Feb. 6, 2024

(54) FIBERS COMPRISING POLYESTERAMIDE COPOLYMERS FOR DRUG DELIVER

(71) Applicant: DSM IP Assets B.V., Heerlen (NL)

(72) Inventors: Mirian Hendrika Jacoba Gillisen-Van Der Vight, Echt (NL); Jens Christoph Thies, Echt (NL); Gueorgui Mihov, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 171 days.

This patent is subject to a terminal disclaimer.

(21) Appl. No.: 17/381,320

(22) Filed: Jul. 21, 2021

(65) Prior Publication Data

US 2022/0002912 A1 Jan. 6, 2022

Related U.S. Application Data

(60) Division of application No. 16/689,569, filed on Nov. 20, 2019, now abandoned, which is a continuation of
(Continued)

(30) Foreign Application Priority Data

Oct. 24, 2012 (EP) ..................................... 12189803
May 7, 2013 (EP) ..................................... 13166874

(51) Int. Cl.
*D01F 6/82* (2006.01)
*A61K 47/34* (2017.01)
(Continued)

(52) U.S. Cl.
CPC .............. *D01F 6/82* (2013.01); *A61K 9/0048* (2013.01); *A61K 9/70* (2013.01); *A61K 47/34* (2013.01); *C08G 69/44* (2013.01); *C08L 77/12* (2013.01)

(58) Field of Classification Search
CPC ........... D01F 6/82; C08G 69/44; A61K 47/34; A61K 9/0048; A61K 9/70
See application file for complete search history.

(56) References Cited

U.S. PATENT DOCUMENTS 10,538,864 B2 * 1/2020 Gillissen-Van Der Vight ............. A61K 9/0048

FOREIGN PATENT DOCUMENTS

WO WO-2012150255 A1 * 11/2012 ......... A61K 31/4535
WO WO-2012175746 A1 * 12/2012 ........... A61K 31/165

OTHER PUBLICATIONS

"Syringe Needle Conversion Chart" (available at https://www.sigmaaldrich.com/deepweb/assets/sigmaaldrich/product/documents/374/803/syringes.pdf) (Year: 2023).*

* cited by examiner

Primary Examiner — Sean M Basquill
(74) Attorney, Agent, or Firm — Kevin M. Bull (57) ABSTRACT

The present invention relates to fibers comprising a polyesteramide (PEA) having a chemical formula described by structural formula (IV), Formula (IV)

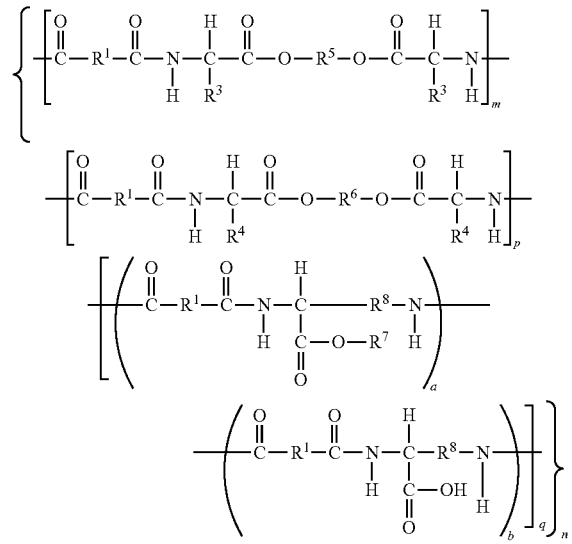

wherein
m+p varies from 0.9-0.1 and q varies from 0.1 to 0.9;
m+p+q=1 whereby m or p could be 0;
n is about 5 to about 300; (pref. 50-200);
—$R_1$ is independently selected from the group consisting of ($C_2$-$C_{20}$) alkylene, ($C_2$-$C_{20}$) alkenylene, —($R_9$—CO—O—$R_{10}$—O—CO—$R_9$)—, —$CHR_{11}$—O—CO—$R_{12}$—$COOCR_{11}$—, and combinations thereof;
—$R_3$ and $R_4$ in a single backbone unit m or p, respectively, are independently selected from the group consisting of hydrogen, ($C_1$-$C_6$)alkyl, ($C_2$-$C_6$)alkenyl, ($C_2$-$C_6$)alkynyl, ($C_6$-$C_{10}$)aryl, ($C_1$-$C_6$)alkyl, —($CH_2$)SH, —($CH_2$)$_2$S($CH_3$), —$CH_2$OH, —CH(OH)$CH_3$, —($CH_2$)$_4$$NH_3$+, —($CH_2$)$_3$NHC(=NH$_2$+)$NH_2$, —$CH_2$COOH, —($CH_2$)COOH, —$CH_2$—CO—$NH_2$, —$CH_2$CH—CO—$NH_2$, —$CH_2$$CH_2$COOH, $CH_3$—$CH_2$—CH($CH_3$)—, ($CH_3$)$_2$—CH—$CH_2$—, $H_2$N—($CH_2$)$_4$—, Ph-$CH_2$, CH=C—$CH_2$, HO-p-Ph-$CH_2$, ($CH_3$)$_2$—CH—, Ph-NH—, NH—($CH_2$)$_3$—C—, NH—CH=N—CH=C—$CH_2$—;

(Continued)

—$R_5$ is selected from the group consisting of $(C_2$-$C_{20})$ alkylene, $(C_2$-$C_{20})$alkenylene, alkyloxy or oligoethyleneglycol;

—$R_6$ is selected from bicyclic-fragments of 1,4:3,6-dianhydrohexitols of structural formula (III);

Formula III

—$R_7$ is selected from the group consisting of $(C_6$-$C_{10})$ aryl$(C_1$-$C_6)$alkyl;

—$R_8$ is —$(CH_2)4$—;

—$R_9$ or $R_{10}$ are independently selected from $C_2$-$C_{12}$ alkylene or $C_2$-$C_{12}$ alkenylene; and —$R_{11}$ or $R_{12}$ are independently selected from H, methyl, $C_2$-$C_{12}$ alkylene or $C_2$-$C_{12}$ alkenylene whereby a is at least 0.05 and b is at least 0.05 and a+b=1.

20 Claims, 5 Drawing Sheets

Related U.S. Application Data application No. 14/432,349, filed as application No. PCT/EP2013/072274 on Oct. 24, 2013, now Pat. No. 10,538,864.

(60) Provisional application No. 61/717,806, filed on Oct. 24, 2012.

(51) Int. Cl.

| | |
|---|---|
| *A61K 9/00* | (2006.01) |
| *C08G 69/44* | (2006.01) |
| *C08L 77/12* | (2006.01) |
| *A61K 9/70* | (2006.01) |

In-vitro degradation, weight loss

FIBERS COMPRISING POLYESTERAMIDE COPOLYMERS FOR DRUG DELIVER

CROSS-REFERENCE TO RELATED APPLICATIONS

This application is a Divisional of U.S. patent application Ser. No. 16/689,569, now abandoned, which is a Continuation of U.S. patent application Ser. No. 14/432,349, now U.S. Pat. No. U.S. Ser. No. 10/538,864; which is a US National Phase application of International Application PCT/EP2013/072274, filed 24 Oct. 2013, which designated the US and claims priority to European Patent Application No. EP12189803.5, filed 24 Oct. 2012, U.S. Provisional Patent Application No. 61/717,806, filed 24 Oct. 2012, and European Patent Application No. EP13166874.1, filed 7 May 2013, the entire contents of each of which are hereby incorporated by reference.

BACKGROUND

The present invention relates to fibers comprising polyesteramide co-polymers. The present invention also relates to the fibers for use in medical applications especially for use in the delivery of bioactive agents.

Biodegradable polyesteramides are known in the art, in particular α-amino acid-diol-diester based polyesteramides (PEA) are known from G. Tsitlanadze, et al. J. Biomater. Sci. Polym. Edn. (2004) 15:1-24. These polyesteramides provide a variety of physical and mechanical properties as well as biodegradable profiles which can be adjusted by varying three components in the building blocks during their synthesis: naturally occurring amino acids and, therefore, hydrophobic alpha-amino adds, non-toxic fatty diols and aliphatic dicarboxylic acids.

WO2002/18477 specifically refers to alpha-amino acid-diol-diester based polyesteramides (PEA) copolymers of formula I, further referred to as PEA-I, Formula I wherein:
m varies from 0.1 to 0.9; p varies from 0.9 to 0.1; n varies from 50 to about 150;
each R1 is independently ($C_1$-$C_{20}$)alkylene;
each $R_2$ is independently hydrogen or ($C_6$-$C_{10}$)aryl(C1-$C_6$)alkyl;
each $R_3$ is independently hydrogen, (C1-$C_6$) alkyl, ($C_2$-$C_6$)alkenyl, ($C_2$-$C_6$)alkynyl, or ($C_6$-$C_{10}$)aryl(C1-$C_6$)alkyl; and
each $R_4$ is independently ($C_2$-$C_{20}$)alkylene.

PEA-I is a random copolymer comprising m units build upon alpha-amino acids, diols and an aliphatic dicarboxylic acids, which are copolymerized with p units build upon an aliphatic dicarboxylic acid and L-lysine.

WO2007035938 discloses another type of random PEA co-polymers according to Formula II comprising at least two linear saturated or unsaturated aliphatic diol residues into two bis-(a amino acid)-based diol-diesters.

Formula II wherein
m is 0.01 to 0.99; p is 0.99 to 0.01; and q is 0.99 to 0.01; and wherein n is 5 to 100; wherein
—$R_1$ can be independently selected from the group consisting of ($C_2$-$C_{20}$)alkylene, ($C_2$-$C_{20}$)alkenylene, —($R_9$—CO—O—$R_{10}$—O—CO—$R_9$)—, —$CHR_{11}$—O—CO—$R_{12}$COOCR$_{11}$— and combinations thereof;
—$R_3$ and $R_4$ in a single co-monomer m or p, respectively, can be independently selected from the group consisting of hydrogen, ($C_1$-$C_6$)alkyl, ($C_2$-$C_6$)alkenyl, ($C_2$-$C_6$) alkynyl. ($C_6$-$C_{10}$)aryl, ($C_1$-$C_6$)alkyl, —($CH_2$)SH, —($CH_2$)$_2$S($CH_3$), —$CH_2$OH, —CH(OH)$CH_3$, —($CH_2$)$_4$$NH_2$+, —($CH_2$)$_3$NHC(=$NH_2$+)$NH_2$, —$CH_2$COOH, —($CH_2$)COOH, —$CH_2$CO—$NH_2$, —$CH_2$$CH_2$—CO—$NH_2$, —$CH_2$$CH_2$COOH, $CH_3$—$CH_2$—CH($CH_3$)—, ($CH_3$)$_2$CH—$CH_2$—, $H_2$N—($CH_2$)$_4$—, Ph-$CH_2$, CH=C—$CH_2$—, HO-p-Ph-$CH_2$—, ($CH_3$)$_2$—CH—, Ph-NH—, NH—($CH_2$)$_3$—C—, NH—CH=N—CH=C—$CH_2$—;

—R₅ is can be selected from the group consisting of $(C_2-C_{20})$alkylene, $(C_2-C_{20})$alkenylene, alkyloxy or oligoethyleneglycol;

—R₆ can be selected from bicyclic-fragments of 1,4:3,6-dianhydrohexitols of structural formula (III); cycloalkyl fragments such as 1,4-cyclohexane diol derivative, aromatic fragments or heterocyclic fragments such as hexose derived fragments;

Formula III

—R₇ can be hydrogen, $(C_6-C_{10})$ aryl, $(C_1-C_6)$ alkyl or a protecting group such as benzyl- or a bioactive agent;
—R₈ can be independently $(C_1-C_{20})$ alkyl or $(C_2-C_{20})$ alkenyl;
—R₉ or R₁₀ can be independently selected from $C_2-C_{12}$ alkylene or $C_2-C_{12}$ alkenylene; and
—R₁₁ or R₁₂ can be independently selected from H, methyl, $C_2-C_{12}$ alkylene or $C_2-C_{12}$ alkenylene.

SUMMARY

However, in some medical areas there is a need for polymers and drug delivery forms such as fibers comprising polymers which degrade hydrolytically instead of enzymatically. This need exists for example in ophthalmology where the delivery of drugs intra-ocularly is a particular problem. The eye is divided into two chambers; the anterior segment which is the front of the eye, and the posterior segment which is the back of the eye. In the back of the eye, in the vitreous, less or no enzymes are present such that for example fibers or rods based on enzymatically degradable polyesteramides will not degrade or will degrade too slow. Any of these two events will compromise the fiber degradability in-vivo and respectively the fiber as biodegradable drug elution system for medical applications.

There is thus still a need in the art for a fiber as delivery system comprising biodegradable polyesteramides which provide for continuous delivery of bioactive agents over a sustained period of time.

The object of the present invention is therefore to provide fibers comprising biodegradable polyesteramide copolymers which take away the mentioned disadvantages associated with fiber degradation.

The object of the present invention is achieved by providing fibers comprising a biodegradable poly(esteramide) copolymer (PEA) according to structural formula (IV),

Formula (IV)

If in the random polyesteramide co-polymer of Formula (II) m+p+q=1, q=0.25, p=0.45 whereby R₁ is —(CH₂)₈; R₃ and R₄ in the backbone units m and p is leucine, —R₅ is hexane, and R₆ is a bicyclic-fragments of 1,4:3,6-dianhydrohexitols of structural formula (III); R₇ is benzyl group and R₈ is —(CH₂)4— this polyesteramide is further referred to as PEA-III-Bz. In case that R₇ is H, the polyesteramide is further referred to as PEA-III-H. In case that m+p+q=1, q=0.25, p=0.75 and m=0, whereby R₁ is —(CH₂)₄; R₃ is (CH₃)₂—CH—CH₂—, R₇ is benzyl, R₈ is —(CH₂)₄; and R₆ is selected from bicyclic-fragments of 1.4:3,6-dianhydrohexitols of structural formula (III), the polyesteramide is further referred to as PEA-IV-Bz, in case that R₇ is H the polyesteramide is further referred to as PEA-IV-H.

The polyesteramides facilitate the in vivo release of bioactive agents dispersed in the polymer at a controlled release rate, which is specific and constant over a prolonged period. It is furthermore disclosed that the PEA polymers break down in vivo via enzymes to produce natural α-amino acids among the break down products which are substantially non-inflammatory.

wherein
m+p varies from 0.9-0.1 and q varies from 0.1 to 0.9;
m+p+q=1 whereby m or p could be 0;
n is about 5 to about 300;
—R₁ is independently selected from the group consisting of $(C_2-C_{20})$ alkylene, $(C_2-C_{20})$ alkenylene, —(R₉—CO—O—R₁₀—O—CO—R₉)—, —CHR₁₁—O—CO—R₁₂—COOCR₁₁—, and combinations thereof;
—R₃ and R₄ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —(CH₂)SH, —(CH₂)₂S(CH 3), —CH₂OH, —CH(OH)CH₃, —(CH₂)₄NH₃+,
—(CH₂)₃NHC(=NH₂+)NH₂, —CH₂COOH, —(CH₂)COOH, —CH₂—CO—NH₂, —CH₂CH₂—CO—NH₂, —CH₂CH₂COOH, CH₃—CH₂—CH(CH₃)—, (CH₃)₂—CH—CH₂—, H₂N—(CH₂)₄—, Ph-CH₂—, CH=C—CH₂—, HO-p-Ph-CH₂—, (CH₃)₂CH—, Ph-NH—, NH—(CH₂)₃—C—, NH—CH=N—CH=C—CH₂—;
—R₅ is selected from the group consisting of $(C_2-C_{20})$ alkylene, $(C_2-C_{20})$alkenylene, alkyloxy or oligoethyleneglycol;

—$R_6$ is selected from bicyclic-fragments of 1,4:3,6-dianhydrohexitols of structural formula (III); cycloalkyl fragments such as 1,4-cyclohexane diol derivative, aromatic fragments or heterocyclic fragments such as hexose derived fragments;

Formula III

—$R_7$ is selected from the group consisting of ($C_6$-$C_{10}$) aryl($C_1$-$C_6$) alkyl;
—$R_8$ is —$(CH_2)_4$—;
—$R_9$ or $R_{10}$ are independently selected from $C_2$-$C_{12}$ alkylene or $C_2$-$C_{12}$ alkenylene;
—$R_{11}$ or $R_{12}$ are independently selected from H, methyl, $C_2$-$C_{12}$ alkylene or $C_2$-$C_{12}$ alkenylene whereby a is at least 0.05, b is at least 0.05 and a+b=1.

Surprisingly it has been found that fibers comprising the biodegradable polyesteramides of formula (IV) in which both L-Lysine-H as well L-lysine-benzyl are present, (hereinafter referred to as PEA-H/Bz) provide unexpected properties in terms of release and degradation. It has been found that fibers comprising PEA-H/Bz co-polymers provide a sustained release of bioactive agents and degrade hydrolytically at physiological conditions via bulk erosion mechanism in contrast with the PEA polymers known in the prior art that degrade only in presence of certain classes of enzymes by surface erosion.

The degradation properties of the fibers comprising the PEA-H/Bz co-polymers according to the present invention are markedly different than the degradation properties of prior art polymers such as the above named PEA-I, PEA-III, PEA-IV or polyesters for example poly-lactide-glycolide copolymers (PLGA) or polylactide (PLLA). It has been found that fibers comprising the PEA-H/Bz co-polymers seem to degrade hydrolytically and mainly via bulk erosion mechanism whereas the known PEA's degrade mainly via an enzymatic degradation process and via a surface erosion mechanism.

A further disadvantage in the degradation of for example PLGA and PLLA fibers is the fact that they often result in a pH drop which is undesired because it may influence the stability of the bioactive agent to be released from the fibers trigger inflammatory response. It is well known that during degradation of PLGA fibers highly acidic degradation products are formed resulting in pH drop. In contrast the pH of the PEA-III-H/Bz fibers does not change under analogous conditions. It seems that lysine free carboxylic groups and acidic species generated during the degradation are in a right balance to catalyze bond cleavage along the polyesteramide chain but not compromising the optimal physiological conditions. From experiments it has been found that fibers of PEA-H/Bz do not show a significant pH drop.

The above findings confirm that fibers comprising the polyesteramides of formula IV in which both L-Lysine-H as well L-lysine-benzyl are present in a certain ratio provides surprising properties addressing better the needs of fibers or rods in drug delivery.

DETAILED DESCRIPTION

In the following embodiments of the present invention n in Formula (IV) preferably varies from 50-200 and a may be at least 0.15, more preferably at least 0.5, most preferably 0.75, even more preferably at least 0.8.

In one embodiment the fibers comprising the biodegradable polyesteramide copolymer according to Formula (IV) comprise p=0 and m+q=1 whereby m=0.75, a=0.5 and a+b=1, $R_1$ is $(CH_2)_8$, $R_3$ is —$(CH_3)_2$—CH—$CH_2$—, $R_5$ is hexyl, $R_7$ is benzyl and $R_8$ is —$(CH_2)_4$—. This polyesteramide is referred to as PEA-I-H/Bz 50% H.

In another preferred embodiment of the present invention the fibers comprising the biodegradable polyesteramide copolymer according to Formula (IV) comprise m+p+q=1, q=0.25, p=0.45 and m=0.3 whereby a is 0.5 and a+b=1 and whereby $R_1$ is —$(CH_2)_8$; $R_3$ and $R_4$ respectively are —$(CH_3)_2$—CH—$CH_2$—, $R_5$ is selected from the group consisting of ($C_2$-$C_{20}$)alkylene, $R_6$ is selected from bicyclic-fragments of 1,4:3,6-dianhydrohexitols of structural formula (III); $R_7$ is benzyl and $R_8$ is —$(CH_2)_4$. This polyesteramide is referred to as PEA-III-H/Bz 50% H.

In a still further preferred embodiment of the present invention fibers comprising the biodegradable polyesteramide copolymer according to Formula (IV) comprise m+p+q=1, q=0.25, p=0.45 and m=0.3 whereby a is 0.75 and a+b=1, $R_1$ is —$(CH_2)_8$; $R_4$ is $(CH_3)_2$—CH—$CH_2$—, $R_7$ is benzyl, $R_8$ is —$(CH_2)_4$— and $R_6$ is selected from bicyclic fragments of 1,4:3,6-dianhydrohexitols of structural formula (III). This polyesteramide is referred to as PEA-III-H/Bz 25% H.

In a yet further preferred embodiment of the present invention the fibers comprising the biodegradable poly(esteramide) copolymer according to Formula (IV) comprise m+p+q=1, q=0.1, p=0.30 and m=0.6 whereby a=0.5 and a+b=1. $R_1$ is —$(CH_2)_4$; $R_3$ and $R_4$ respectively, are $(CH_3)_2$—CH—$CH_2$—; $R_6$ is selected from the group consisting of ($C_2$-$C_{20}$)alkylene, $R_7$ is benzyl, $R_8$ is —$(CH_2)_4$— and $R_6$ is selected from bicyclic-fragments of 1,4:3,6-dianhydrohexitols of structural formula (III). This polyesteramide is referred to as PEA-II-H/Bz50% H.

As used herein, the term "alkyl" refers to a monovalent straight or branched chain hydrocarbon group including methyl, ethyl, n-propyl, isopropyl, n-butyl, isobutyl, tert-butyl, n-hexyl, and the like.

As used herein, the term "alkylene" refers to a divalent branched or unbranched hydrocarbon chain such as —$CH_2$—, —$(CH_2)_2$—, —$(CH_2)_3$—, —$(CH_2)_4$—, —$(CH_2)_5$— and the like.

As used herein, the term "alkenyl" refers to a monovalent straight or branched chain hydrocarbon group containing at least one unsaturated bond in the main chain or in a side chain.

As used herein, "alkenylene", refers to structural formulas herein to mean a divalent branched or unbranched hydrocarbon chain containing at least one unsaturated bond in the main chain or in a side chain.

As used herein, "alkynyl", refers to straight or branched chain hydrocarbon groups having at least one carbon-carbon triple bond.

The term "aryl" is used with reference to structural formulas herein to denote a phenyl radical or an ortho-fused bicyclic carbocyclic radical having about nine to ten ring atoms in which at least one ring is aromatic. Examples of aryl include, but are not limited to, phenyl, naphthyl, and nitrophenyl.

The term "biodegradable" refers to material which is capable of being completely or substantially degraded or eroded when exposed to an in vivo environment or a representative in vitro. A polymer is capable of being degraded or eroded when it can be gradually broken-down, resorbed, absorbed and/or eliminated by, for example, hydrolysis, enzymolysis, oxidation, metabolic processes, bulk or surface erosion, and the like within a subject. The terms "bioabsorbable" and "biodegradable" are used interchangeably in this application.

As used herein, fibers include also rods or wires.

At least one of the alpha-amino acids used in the polyesteramide co-polymers according to formula (IV) is a natural alpha-amino acid. For example, when the R3s or R4s are benzyl the natural alpha-amino acid used in synthesis is L-phenylalanine. In alternatives wherein the $R_3$s or $R_4$s are —$CH_2$—$CH(CH_3)_2$, the co-polymer contains the natural amino acid, leucine. By independently varying the $R_3$s and $R_4$s within variations of the two co-monomers as described herein, other natural alpha-amino acids can also be used, e.g., glycine (when the $R_3$ or $R_4$ are H), alanine (when the $R_3$ or $R_4$ are $CH_3$), valine (when the $R_3$ or $R_4$ are —$CH(CH_3)_2$, isoleucine (when the $R_3$ or $R_4$ are —$CH(CH_3)$—$CH_2$—$CH_3$), phenylalanine (when the $R_3$ or $R_4$ are $CH_2$—$C_6H_5$), lysine (when the $R_3$ or $R_4$ ($CH_2)_4$—$NH_2$); or methionine (when the $R_3$s or $R_4$s are —$(CH_2)_2S(CH_3)$, and mixtures thereof.

The polyesteramide co-polymers of Formula (IV) preferably have an average number molecular weight (Mn) ranging from 15,000 to 200,000 Daltons. The polyesteramide co-polymers described herein can be fabricated in a variety of molecular weights and a variety of relative proportions of the m, p, and q units in the backbone. The appropriate molecular weight for a particular use is readily determined by one skilled in the art. A suitable Mn will be in the order of about 15,000 to about 100,000 Daltons, for example from about 30,000 to about 80,000 or from about 35,000 to about 75,000. Mn is measured via GPC in THF with polystyrene as standard.

The basic polymerization process of polyesteramides is based on the process described by G. Tsitlanadze, et al. J. Biomater. Sci. Polym. Edn. (2004) 15:1-24, however different building blocks and activating groups were used.

The polyesteramides of Formula (IV) are for example synthesized as shown in scheme 1; via solution polycondensation of para-toluene sulfonate di-amines salts (X1, X2, X3) with activated di-acids (Y1). Typically, dimethylsulfoxide or dimethylformamide is used as solvent. Typically, as a base triethylamide is added, the reaction is carried out under an inert atmosphere at 60° C. for 24-72 hours under constant stirring. Subsequently the obtained reaction mixture is purified via a water precipitation followed by an organic precipitation and filtration. Drying under reduced pressure yields the polyesteramide.

Scheme 1: schematic representation of PEA polymerization process, including some typical monomers.

-continued

Typically, the average diameter of the fibers is between 50 and 1000 micrometer. The preferred average diameter depends on the intended use. For instance, in case the fibers are intended for use as an injectable drug delivery system, in particular as an ocular drug delivery system, an average diameter of 50-500 μm may be desired, more preferably an average diameter of 100-300 μm may be desired.

The fibers of the present invention may be used as a delivery system for bioactive agents but also for the delivery of diagnostic aids or imaging agents.

The fibers according to the present invention may comprise one or more bioactive agents. The bioactive agent(s) may be more or less homogeneously dispersed within the fibers.

In particular, the bioactive agent may be selected from the group of nutrients, pharmaceuticals, small molecule drugs, proteins, peptides, vaccines, genetic materials, (such as polynucleotides, oligonucleotides, plasmids, DNA and RNA), diagnostic agents, and imaging agents. The bioactive agent, such as an bioactive pharmacologic ingredient (API), may demonstrate any kind of activity, depending on the intended use.

The bioactive agent may be capable of stimulating or suppressing a biological response. The bioactive agent may for example be chosen from growth factors (VEGF, FGF, MCP-1, PlGF, antibiotics (for instance penicillin's such as B-lactams, chloramphenicol), anti-inflammatory compounds, antithrombogenic compounds, anti-claudication drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signalling molecules and psychoactive medicaments.

The bioactive agents can have antiproliferative or anti-inflammatory properties or can have other properties such as antineoplastic, antiplatelet, anti-coagulant, anti-fibrin, antithrombotic, antimitotic, antibiotic, antiallergic, or antioxidant properties. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack NJ.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacydin and prostacydin analogues, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, NJ), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-I-oxyl (4-amino-TEMPO), estradiol, anticancer agents, dietary supplements such as various vitamins, and a combination thereof. Examples of anti-inflammatory agents including steroidal and nonsteroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck AND Co., Inc., Whitehouse Station, NJ). An example of an antiallergic agent is permirolast potassium. Other therapeutic substances or agents which may be appropriate include alpha-interferon, pimecrolimus, imatinib mesylate, midostaurin, and genetically engineered epithelial cells.

Further examples of specific bioactive agents are neurological drugs (amphetamine, methylphenidate), alpha1 adrenoceptor antagonist (prazosin, terazosin, doxazosin, ketanserin, urapidil), alpha2 blockers (arginine, nitroglycerin), hypotensive (clonidine, methyldopa, moxonidine, hydralazine minoxidil), bradykinin, angiotensin receptor blockers (benazepril, captopril, cilazapril, enalapril, fosinopril, lisinopril, perindopril, quinapril, ramipril, trandolapril, zofenopril), angiotensin-1 blockers (candesartan, eprosartan, irbesartan, losartan, telmisartan, valsartan), endopeptidase (omapatrilate), beta2 agonists (acebutolol, atenolol, bisoprolol, celiprolol, esmodol, metoprolol, nebivolol, betaxolol), beta2 blockers (carvedilol, labetalol, oxprenolol, pindolol, propanolol) diuretic actives (chlortalidon, chlorothiazide, epitiazide, hydrochlorothiazide, indapamide, amiloride, triamterene), calcium channel blockers (amlodipin, bamidipin, diltiazem, felodipin, isradipin, lacidipin, lercanidipin, nicardipin, nifedipin, nimodipin, nitrendipin, verapamil), anti arthymic active (amiodarone, solatol, diclofenac, flecainide) or ciprofloxacin, latanoprost, flucloxacillin, rapamycin and analogues and limus derivatives, paclitaxel, taxol, cyclosporine, heparin, corticosteroids (triamcinolone acetonide, dexamethasone, fluocinolone acetonide), anti-angiogenic (iRNA, VEGF antagonists: bevacizumab, ranibizumab, pegaptanib), growth factor, zinc finger transcription factor, triclosan, insulin, salbutamol, oestrogen, norcanthardin, microlidil analogues, prostaglandins, statins, chondroitinase, diketopiperazines, macrocycli compounds, neuregulins, osteopontin, alkaloids, immuno suppressants, antibodies, avidin, biotin, clonazepam. The foregoing substances can also be used in the form of prodrugs or co-drugs thereof. The foregoing substances also include metabolites thereof and/or prodrugs of the metabolites. The foregoing substances are listed by way of example and are not meant to be limiting.

In accordance with the present invention, if a bioactive agent is present, the concentration of one or more bioactive agent(s) in the fibers can be determined by the therapeutic window of the treated medical indication as well as by an administration method. The concentration of one or more bioactive agent(s) in the fibers, can be at least 1 wt %, based on the total weight of the fibers, in particular at least 5 wt. %, more in particular at least 10 wt %. The concentration may be up to 90 wt %, up to 70 wt %, up to 50 wt. % or up to 30 wt. %, as desired.

In addition to the biodegradable polyesteramides as represented by formula IV, the fibers of the present invention may further comprise one or more other polymers selected from the group of biocompatible polymers.

Examples of biocompatible polymers are poly(ortho esters), poly(anhydrides), poly(D,L-lactic acid), poly (L-lactic acid), poly(glycolic acid), copolymers of poly(lactic) and glycolic acid, poly(L-lactide), poly(D,L-lactide), poly(glycolide), poly(D,L-lactide-co-glycolide), poly(L-lactide-co-glycolide), poly(phospho esters), poly(trimethylene carbonate), poly(oxa-esters), poly(oxa-amides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly (ethylene glycol) (PEG), or combinations thereof.

The fiber is preferably manufactured via an extrusion process for example melt extrusion in which the biodegradable polymer and eventual additional compounds are homogenized using a Retsch cryomill. The resulting powder is then filled into a pre-heated DSM Xplore micro-extruder with 5 cc barrel size and twin-screws which are connected to a micro fiber spin device. The biodegradable polymer preferably has a residence time of 5-10 min at 120° C.-140° C. before it is to be stretched into a fiber with diameter in the range of 100-250 μm. The extrusion is normally performed under inert atmosphere in order to minimize the oxidative degradation of the polymer during the process. Under tension it is subsequently cooled at room temperature. The obtained fiber is then preferably cut into pieces from for example 4 mm and may be sterilized via gamma radiation.

The fibers according to the present invention which can be obtained via extrusion do re-model upon exposure to aqueous environment reducing significantly their length and increasing in diameter. The total volume of the fibers is preserved. The length of the fiber is typically reduced by factor of 2 to 20.

Alternatively the fibers of the present invention can also be prepared via injection moulding. In this process fibers are formed in an injection moulder at temperature between 50-200° C., preferably between 100-200° C., resulting in fibers with a diameter of approximately 200 μm. Then the mould is cooled to room temperature before opening and the fibers are taken out. Essential for this processing method is that so obtained fibers do not re-model upon exposure to aqueous environment well preserving their length and diameter.

In case that the fibers are loaded with one or more bioactive agents, the loading may be achieved by forming the fibers in the presence of the bioactive agent or thereafter. To achieve fibers with a high amount of bioactive agent, it is generally preferred to prepare the fibers in the presence of the bioactive agent. In particular in the case that the bioactive agent is sensitive it is preferred to load the fibers after they have been formed. This can be achieved by contacting the fibers with the bioactive agent and allowing the bioactive agent to diffuse into the fibers and/or adhere/adsorb to the surface thereof.

In accordance with the invention it is possible to provide fibers with one or more bioactive agents with satisfactory encapsulation efficiency. (i.e. the amount of bioactive agent in the fibers, divided by the amount of active agent used). Depending upon the loading conditions, an efficiency of at least 20%, an efficiency of at least 50%, at least 75% or at least 90% or more is feasible.

The fibers may be incorporated in for example (rapid prototyped) scaffolds, coatings, patches, composite materials, gels, plasters or hydrogels.

The fibers according to the present invention can be injected or implanted.

In a further embodiment, the fibers may be imagable by a specific technique such as MRI, CT, X-ray. The imaging agent can be incorporated inside the fibers or can be coupled onto their surface. A suitable imaging agent is for example gadolinium.

The fibers comprising the polyesteramide copolymers according to the present invention can be used in the medical field especially in drug delivery in the field of management of pain, MSK, ophthalmology, cancer treatment, vaccine delivery compositions, dermatology, cardiovascular field and orthopedics, spinal, intestinal, pulmonary, nasal, or auricular field.

The fiber according to the present invention can be used as a drug eluting vehicle especially for the treatment of disease in ophthalmology.

The present invention will now be described in detail with reference to the following non limiting examples and figures which are by way of illustration only.

EXAMPLES

Materials

Unless specified otherwise, all chemicals were purchased from Sigma-Aldrich. 1H NMR analysis was performed on a Varian nova 300 spectrometer using a 10 mg/ml polymer solution in deuterated DMSO. The used DSC equipment was from Mettler Toledo 822e connected with an Intercooler and an auto robot TS0801RO.

Example 1

Figure 1:
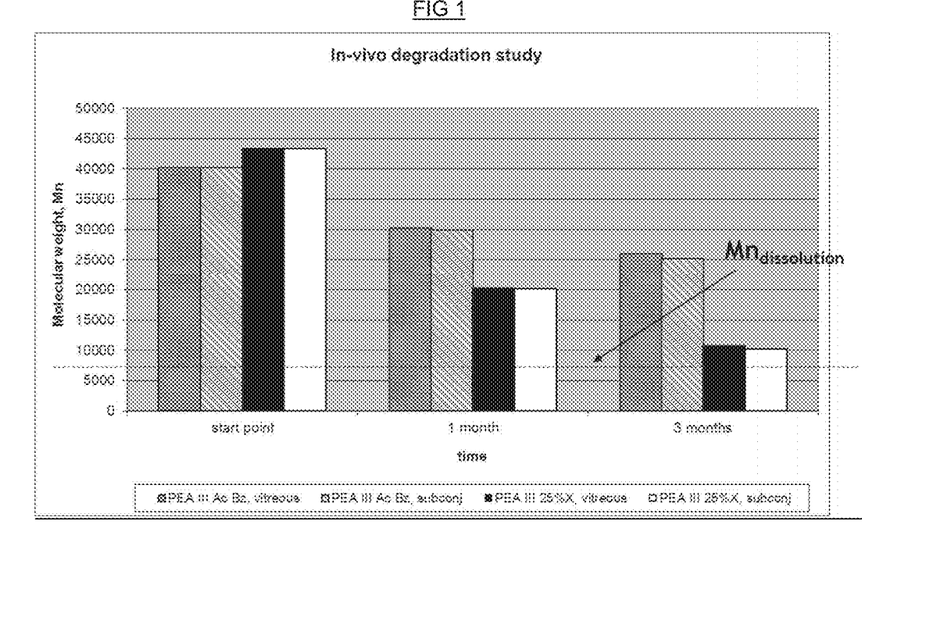
FIG. 1: In vivo degradation of PEA-III-Ac Bz and PEA-III-25% H fibers.
Figure 2:
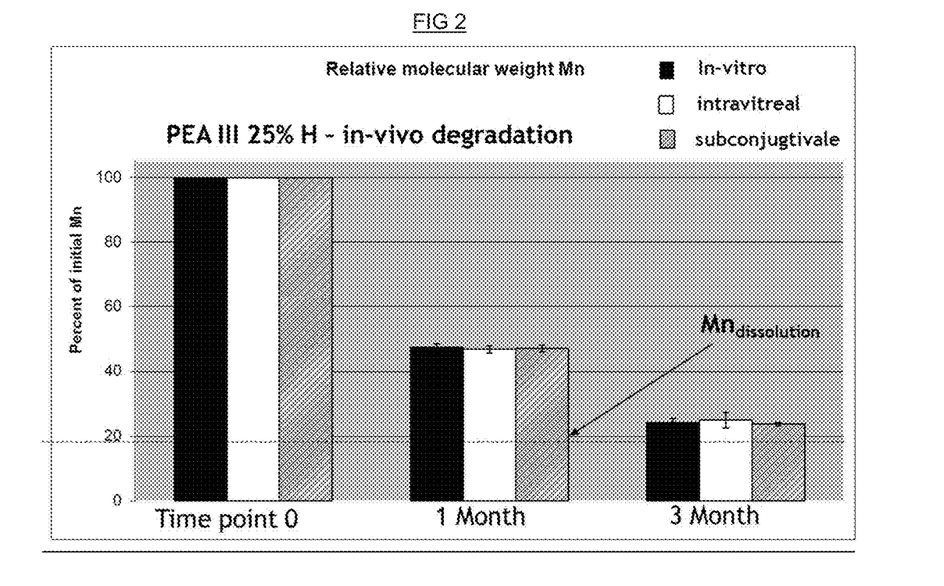
FIG. 2: In vitro/In vivo correlation of degradation of PEA-III-Ac Bz and PEA-III-25% H fibers.
Figure 3:
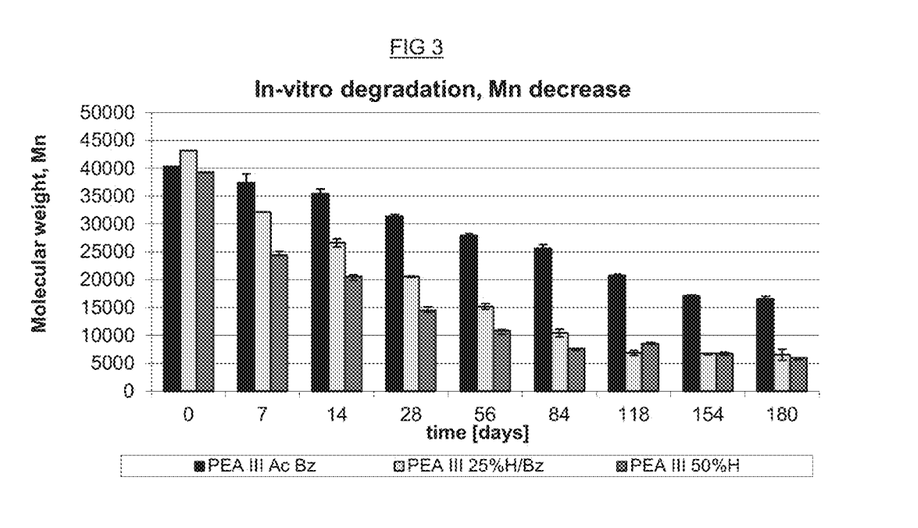
FIG. 3: Molecular weight decrease during hydrolytic degradation in PBS buffer over 180 days
Figure 4:
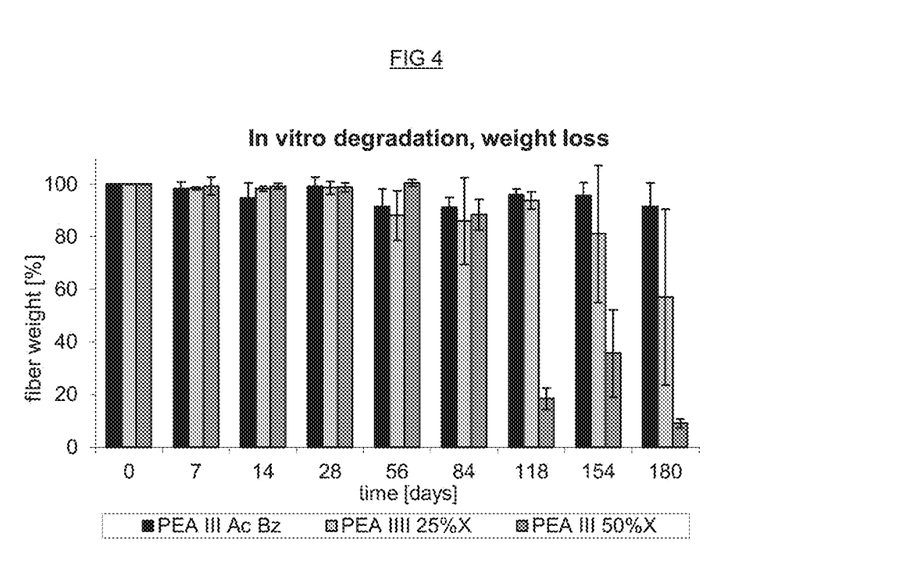
FIG. 4: Weight loss of the fibers during hydrolytic degradation in PBS buffer over 180 days.
Figure 8:
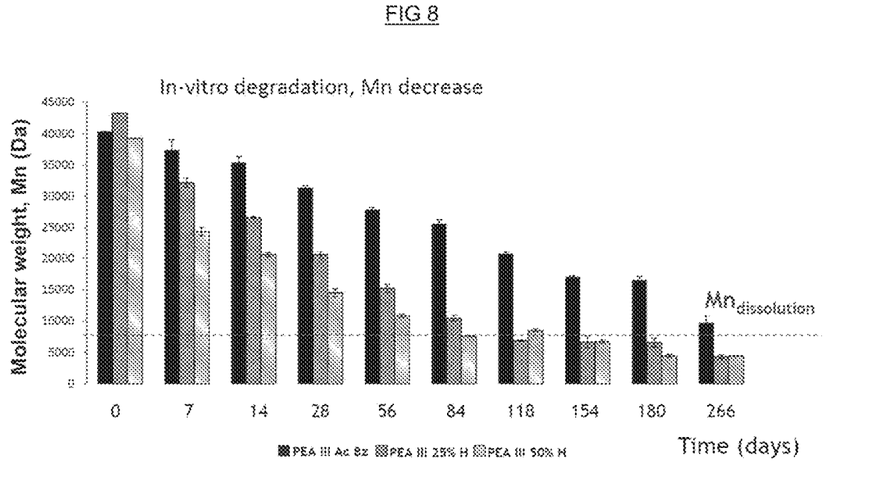
FIG. 8: Molecular weight decrease during hydrolytic degradation in PBS buffer over 266 days.
Figure 9:
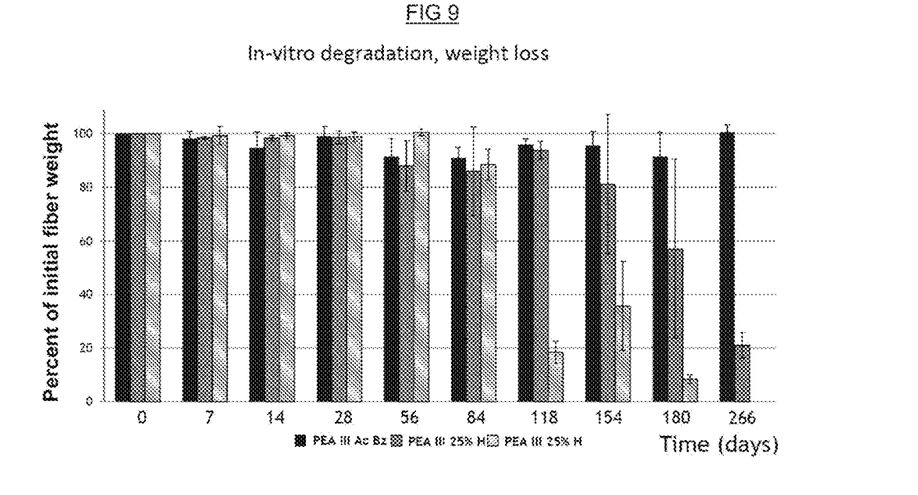
FIG. 9: Weight loss of the fibers during hydrolytic degradation in PBS buffer over 266 days.

Fibers of PEA-III-Ac Bz, PEA-III-H/Bz 25% H and PEA-III-H/Bz 50% H were prepared via extrusion with a diameter of approximately 180 μm. The obtained fibers were cut into pieces with a length of 4-5 mm and were individually weighted on a microbalance. The single fibers were immersed in 3 mL PBS buffer containing 0.05% sodium azide as a biocide. Hydrolytic degradation was performed under gentle orbital shaking at 37° C. Samples were taken in triplicate; the fibers were dried under reduced pressure at 37° C. overnight. The weight of the fibers post degradation was again determined with a microbalance. Relative molecular weights of the remaining polymer fiber were determined using a Waters GPC system consisting of a Waters RI detector type 2414, a Waters separation module with column heater type e2695. The system was equipped with a Styragel HR5E and Styragel HR2 column run at 50° C. As the mobile phase tetrahydrofuran (THF) with a flow rate of 1.0 mL/min was used. Samples were dissolved in 200 μl THF, of which 100 μL was injected onto the column. Evaluation of data was performed with Waters Empower² software. Calculations of molecular weights were relatively to polystyrene standards. Results are represented in FIGS. 3 and 8 which show molecular weight decrease during hydrolytic degradation in PBS buffer over 180 days and 266 days respectively. FIGS. 4 and 9 show the weight loss of the fibers during hydrolytic degradation in PBS buffer over 180 days and over 266 days respectively.

Example 2

The polymers applied were synthesized via polycondensation of pre-calculated amounts of di-p-toluenesulfonicacid salts of bis-(L-leucine) 1,4-dianhydro sorbitol diester, bis-(L-leucine) α,ω-hexane dioldiester, lysine benzyl ester, lysine and di-N-hydroxysuccineimid ester of sebacic acid in anhydrous DMSO and triethylamine added in a glass vessel with overhead stirrer under a nitrogen atmosphere. The usage of pre-activated acid in the reaction allows polymerization at relatively low temperature (65° C.; 48 h) affording side-products free polycondensated and predictable degradation products. The polymers were isolated from the reaction mixture in two precipitation steps to result in white amorphous material of average number molecular weight of 50 kDa as determined by THF based GPC relative to polystyrene standards. The ratio of the different building blocks in the polymer was calculated from the 1H NMR spectrum. Co-polymer composition matched well theoretical prediction. Next the polymers were cryomilled in Retsch ZM200 equipment in presence of 0.20% w/w Chromoionophore II in order to obtain a uniform mixture.

The uniformed cryomilled formulation was processed to fibres at the Pharma mini-extruder with a speed of 1-250 rpm, a temperature range of 140° C., equipped with DSM micro fiber spin device for thin fiber spinning. The polymer had a residence time of 5-10 min at 140° C. before to be stretched into a fiber with diameter in the range of 120-300 μm. The extrusion was performed under inert atmosphere in order to minimize the oxidative degradation of the polymer during the process. The obtained fiber was cut to about 4 mm long and 150 μm in diameter pieces and sterilized via gamma radiation 25 kGy under cooling conditions at BGS, Wiehl, Germany.

Implantation and Clinical Follow Up

Female Chinchilla Bastard rabbits (Charles River Company, Sulzfeld, Germany) with an average body weight of 2-3 kg were used. All animal experiments were conducted in accordance with the principles for the care and use of research animals and were carried out with permission and supervision of the Office for the Nature, Environment and Consumer Protection (LANUV), Recklinghausen, Germany.

For subconjunctival implantation a radial incision was made into the rabbit conjunctiva and a chamber was prepared by dissecting the conjunctiva from the sclera. One dry fiber was placed into the chamber and the incision was closed with one vicryl 9-0 suture. One sample of PEA per eye was implanted. The implant was monitored weekly and read-outs were scheduled after one, three, six, and twelve months.

For intravitreal implantation of dry fibers a customized 26 G intravenous catheter was used. A transscleral paracentesis was made with a 26 G needle 1.5 mm below the limbus and the modified catheter was inserted. After removing the catheter needle the PEA fiber was inserted to the catheter with a micro forceps and moved forward with the catheter needle into the vitreous. The catheter was removed and the intravitreal position of the fiber was documented by video photography. PEA fibers were explanted after 1 and 3 months. Clinical examinations by funduscopy were done weekly to confirm presence and shape of the fibrils and to observe status of the fundus.

After mentioned observation periods eyes were enucleated and macroscopically analyzed. In addition, the explanted fibers were evaluated by weight and GPC in order to assess the changes occurring with the polymer.

Implantation and Clinical Follow Up

Female Chinchilla Bastard rabbits (Charles River Company, Sulzfeld, Germany) with an average body weight of 2-3 kg were used. All animal experiments were conducted in accordance with the principles for the care and use of research animals and were carried out with permission and supervision of the Office for the Nature, Environment and Consumer Protection (LANUV), Recklinghausen, Germany.

For subconjunctival implantation a radial incision was made into the rabbit conjunctiva and a chamber was prepared by dissecting the conjunctiva from the sclera. One dry fiber was placed into the chamber and the incision was closed with one vicryl 9-0 suture. One sample of PEA per eye was implanted. The implant was monitored weekly and read-outs were scheduled after one, three, six, and twelve months.

For intravitreal implantation of dry fibers a customized 26 G intravenous catheter was used. A transscleral paracentesis was made with a 26 G needle 1.5 mm below the limbus and the modified catheter was inserted. After removing the catheter needle the PEA fiber was inserted to the catheter with a micro forceps and moved forward with the catheter needle into the vitreous. The catheter was removed and the intravitreal position of the fiber was documented by video photography. PEA fibers were explanted after 1 and 3 months. Clinical examinations by funduscopy were done weekly to confirm presence and shape of the fibers and to observe status of the fundus.

After mentioned observation periods eyes were enucleated and macroscopically analyzed. In addition, the explanted fibers were evaluated by weight and GPC in order to assess the changes occurring with the polymer.

Example 3

Fibers of PEA-III-H/Bz 25% H were prepared via injection moulding with a diameter of approximately 200 μm. The obtained fibers were cut into pieces with a length of 5-10 mm and were individually weighted on a microbalance. Each individual fiber was imaged using a Motic stereoscope equipped with a Moticam2000 digital camera.

Figure 5:
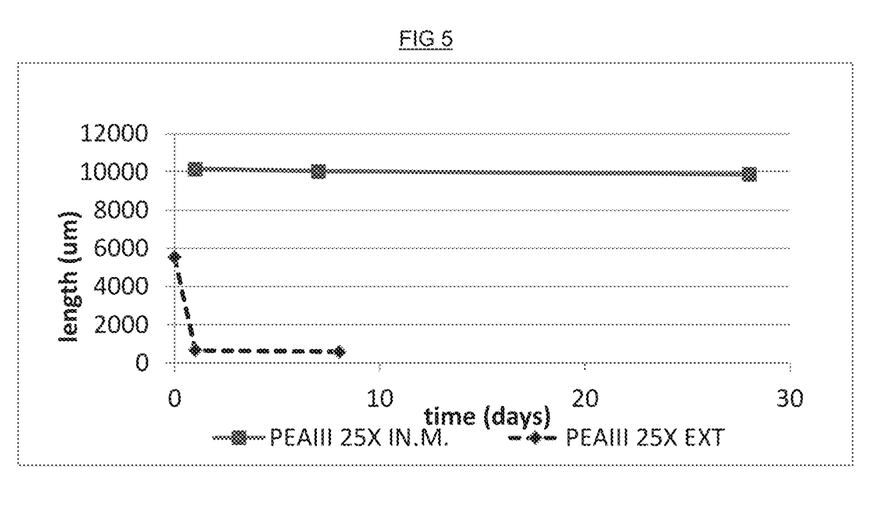
FIG. 5: Evaluation of form stability is graphically represented by fiber length.
Figure 6:
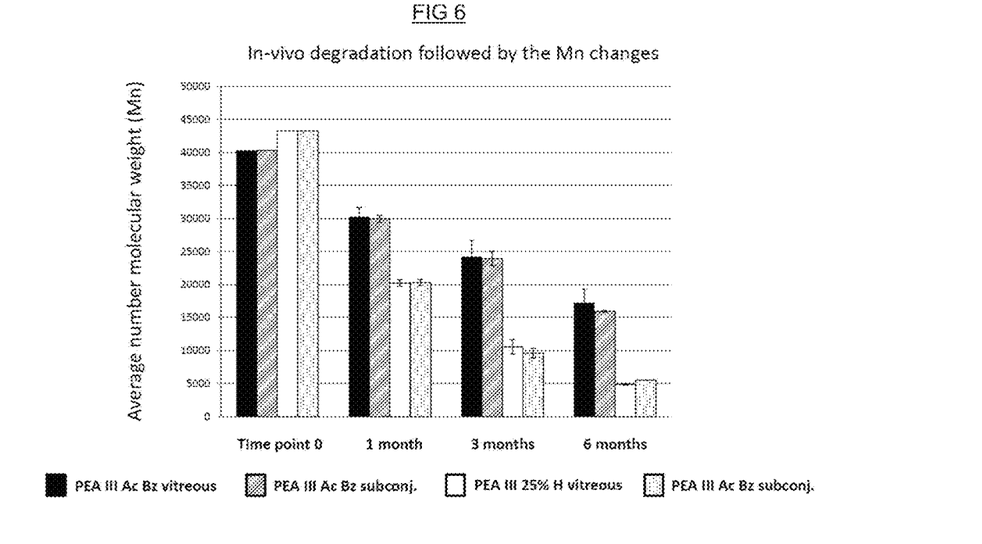
FIG. 6: In vivo degradation of PEA-III-Ac Bz and PEA-III-25% H fibers over 6 months.
Figure 7:
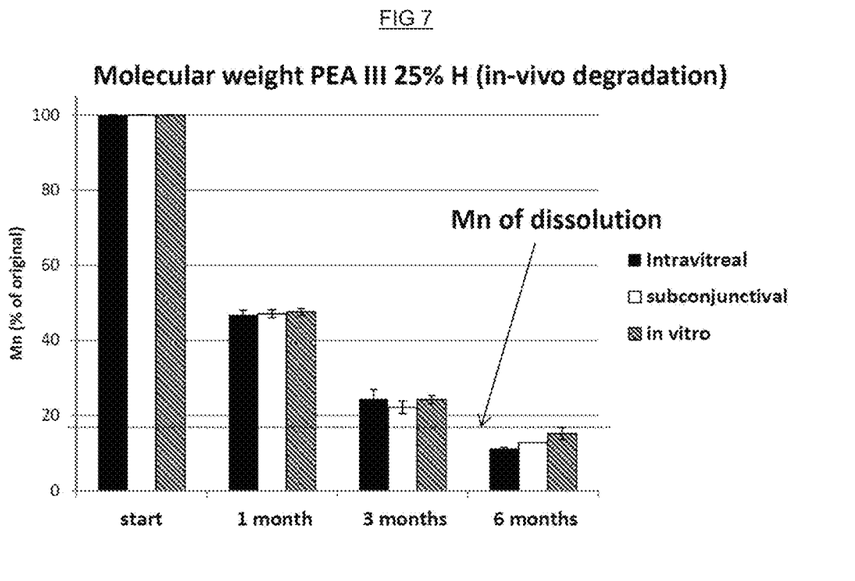
FIG. 7: In vitro/In vivo correlation of degradation of PEA-III-Ac Bz and PEA-III-25% H fibers over 6 months.

Single fibers were immersed in 1 mL PBS buffer and placed on a gentle orbital shaker at 37° C. The experiment was performed in duplicate. At given time points, fibers were gently removed from the buffer and blotted on tissue. Images were taken with the stereoscope and the fiber length and diameter were measured. Buffer was refreshed and the samples were returned to the orbital shaker. In FIG. 5 a calculation of form stability is graphically represented by measuring fiber length. The injection moulded fibers had an initial length of 10 mm and the extruded fiber had initial length of 5 mm. Differences in form stability are clearly expressed by the loss in length of the extruded fiber.

The invention claimed is:

1. A method for treating a condition associated with the eye of a patient comprising the step of implanting a fiber into the eye of the patient, wherein the step of implanting comprises intravitreal or subconjunctival implantation of a fiber having an average diameter between 50 and 500 micrometers, the fiber comprising a bioactive agent dispersed in a biodegradable poly(esteramide) copolymer (PEA) according to structural Formula (IV), Formula (IV)

wherein
m+p is from 0.9 to 0.1 and q is from 0.1 to 0.9;
m+p+q=1, whereby m and p are each greater than 0;
n is about 5 to about 300;
a is at least 0.05, b is at least 0.05, a+b=1, qa=q*a, and qb=q*b; wherein units of m, units of p, units of qa, and units of qb are all randomly distributed throughout the copolymer;
$R_1$ is $(C_2-C_{20})$ alkylene;
$R_3$ and $R_4$ are independently selected from hydrogen, $(C_1-C_6)$alkyl, $(C_2-C_6)$alkenyl, $(C_2-C_6)$alkynyl, $(C_6-C_{10})$aryl, $-CH_2SH$, $-(CH_2)_2S(CH_3)$, $-CH_2OH$, $-CH(OH)CH_3$, $-(CH_2)_4NH_3+$, $-(CH_2)_3NHC(=NH_2+)NH_2$, $-CH_2COOH$, $-CH_2-CO-NH_2$, $-CH_2CH_2-CO-NH_2$, $-CH_2CH_2COOH$, $CH_3-CH_2-CH(CH_3)-$, $(CH_3)_2CH-CH_2-$, $H_2N-(CH_2)_4-$, $Ph-CH_2-$, $CH=C-CH_2-$, $(CH_3)_2CH-$, or $Ph-NH-$;
$R_5$ is $(C_2-C_{20})$alkylene;
$R_6$ is according to structural formula (III);

Formula III $R_7$ is $(C_6-C_{10})$aryl$(C_1-C_6)$alkyl; and
$R_8$ is $-(CH_2)_4-$.

2. The method according to claim 1, wherein a is at least 0.5.

3. The method according to claim 1, wherein a is at least 0.75.

4. The method according to claim 1, wherein a is at least 0.8.

5. The method according to claim 1, wherein n is from 50 to 200, a is at least 0.5.

6. The method according to claim 1, wherein $R_3$ and $R_4$ are independently hydrogen, $(C_1-C_6)$alkyl, $CH_3-CH_2-CH(CH_3)-$, $(CH_3)_2CH-CH_2-$, $Ph-CH_2-$, or $(CH_3)_2CH-$.

7. The method according to claim 1, wherein $R_3$ and $R_4$ are $(CH_3)_2CH-CH_2-$, and $R_7$ is benzyl.

8. The method according to claim 1, wherein $R_1$ is $-(CH_2)_8-$, $R_3$ and $R_4$ are $(CH_3)_2CH-CH_2-$, and $R_7$ is benzyl.

9. The method according to claim 2, wherein $R_3$ and $R_4$ are independently hydrogen, $(C_1-C_6)$alkyl, $CH_3-CH_2-CH(CH_3)-$, $(CH_3)_2CH-CH_2-$, $Ph-CH_2-$, or $(CH_3)_2CH-$.

10. The method according to claim 2, wherein $R_3$ and $R_4$ are $(CH_3)_2CH-CH_2-$, and $R_7$ is benzyl.

11. The method according to claim 5, wherein $R_3$ and $R_4$ are independently hydrogen, $(C_1-C_6)$alkyl, $CH_3-CH_2-CH(CH_3)-$, $(CH_3)_2CH-CH_2-$, $Ph-CH_2-$, or $(CH_3)_2CH-$.

12. The method according to claim 5, wherein $R_3$ and $R_4$ are $(CH_3)_2CH-CH_2-$, and $R_7$ is benzyl.

13. The method according to claim 5, wherein $R_1$ is $-(CH_2)_8-$, $R_3$ and $R_4$ are $(CH_3)_2CH-CH_2-$, and $R_7$ is benzyl.

14. The method according to claim 1, wherein
m=0.3; p=0.45; qa=0.19; and qb=0.06;
$R_1$ is $-(CH_2)_8-$, $R_3$ and $R_4$ are $(CH_3)_2CH-CH_2-$, and $R_7$ is benzyl.

15. The method according to claim 1, wherein the bioactive agent comprises a prostaglandin or a prodrug thereof.

16. The method according to claim 1, wherein the bioactive agent comprises a prostaglandin or a prodrug thereof.

17. The method according to claim 1, wherein the fiber further comprises a poly(ortho ester), poly(anhydride), poly (D,L-lactic acid), poly (L-lactic acid), poly(glycolic acid), copolymers of poly(lactic) and glycolic acid, poly(L-lactide), poly(D,L-lactide), poly(glycolide), poly(D,L-lactide-co-glycolide), or poly(L-lactide-co-glycolide), poly(phospho esters), poly(trimethylene carbonate), poly(oxa-esters), poly(oxa-amides), poly(ethylene carbonate), poly(propylene carbonate), poly(phosphoesters), poly(phosphazenes), poly (tyrosine derived carbonates), poly(tyrosine derived arylates), poly(tyrosine derived iminocarbonates), or combinations thereof.

18. The method according to claim 1, wherein the average diameter of the fiber is from 100 to 300 micrometers.

19. The method according to claim 1, wherein the fiber comprises a first length and first diameter prior to implantation and a second length and second diameter after implantation, wherein the first length is greater than the second length and the first diameter is less than the second diameter.

20. The method according to claim 19, wherein the fiber was formed by an extrusion process comprising stretching a heated composition into a fiber having a diameter of from 100-250 μm and cooling the fiber under tension.

* * * * *